(12) United States Patent
Hopler

(10) Patent No.: US 7,954,945 B2
(45) Date of Patent: Jun. 7, 2011

(54) REFLECTOMETRY/INTERFEROMETRY SYSTEM AND METHOD FOR CORNEAL PLANE POSITIONING

(75) Inventor: Mark D. Hopler, Winter Springs, FL (US)

(73) Assignee: Alcon Refractivehorizons, Inc., Fort Worth, TX (US)

( * ) Notice: Subject to any disclaimer, the term of this patent is extended or adjusted under 35 U.S.C. 154(b) by 0 days.

(21) Appl. No.: 12/612,924

(22) Filed: Nov. 5, 2009

(65) Prior Publication Data

US 2010/0277689 A1 Nov. 4, 2010

Related U.S. Application Data

(63) Continuation of application No. 11/682,608, filed on Mar. 6, 2007, now abandoned.

(51) Int. Cl.
*A61B 3/10* (2006.01)

(52) U.S. Cl. .......................................... 351/205; 351/200

(58) Field of Classification Search .................... 351/205
See application file for complete search history.

(56) References Cited

U.S. PATENT DOCUMENTS

| | | | |
|---|---|---|---|
| 2005/0018137 A1 | 1/2005 | Barth et al. | |
| 2005/0140981 A1 | 6/2005 | Waelti | |
| 2005/0192562 A1* | 9/2005 | Loesel et al. | 606/5 |
| 2005/0203422 A1* | 9/2005 | Wei | 600/476 |
| 2008/0144771 A1 | 6/2008 | Gertner | |

FOREIGN PATENT DOCUMENTS

| WO | 2006/090217 A1 | 8/2006 |
|---|---|---|
| WO | 2007/016231 A1 | 2/2007 |

* cited by examiner

*Primary Examiner* — Ricky L Mack
*Assistant Examiner* — James C Jones
(74) *Attorney, Agent, or Firm* — Armando Pastrana, Jr.

(57) ABSTRACT

A system for positioning an eye of a patient, for example, for laser ophthalmic surgery includes a reflectometer adapted to receive as input a reflected beam from an anterior surface of a cornea of an eye of a patient. The interferometer is calibratable to a desired position of the corneal anterior surface. A comparator is in signal communication with the interferometer and is adapted to calculate from the input a difference between an actual position and the desired position of the corneal anterior surface. A device is in signal communication with the comparator for moving the patient a distance in a direction for matching the actual position to the desired position of the corneal anterior surface.

12 Claims, 3 Drawing Sheets

REFLECTOMETRY/INTERFEROMETRY SYSTEM AND METHOD FOR CORNEAL PLANE POSITIONING

This application is a continuation of U.S. application Ser. No. 11/682,608 filed Mar. 6, 2007 now abandoned.

FIELD OF THE INVENTION

The present invention is directed to patient positioning systems for ophthalmic laser surgery systems, and, in particular, to such systems using reflectometry/interferometry.

BACKGROUND OF THE INVENTION

Precise positioning of a patient's eye is critical for successful outcomes in ophthalmic laser systems. At present such positioning is performed by optimizing the focus of a video image of the patient's eye. Typically such focusing is performed by the surgeon, and can be accurate to the millimeter level.

Therefore, it would be advantageous to provide a system and method that could improve the accuracy of positioning a patient's cornea for ophthalmic surgery, and that could be performed automatically.

SUMMARY OF THE INVENTION

The present invention is directed to a system for positioning an eye of a patient, for example, for laser ophthalmic surgery. The system comprises a reflectometer adapted to receive as input a reflected beam from an anterior surface of a cornea of an eye of a patient. The interferometer is calibratable to a desired position of the corneal anterior surface.

A comparator is in signal communication with the interferometer and is adapted to calculate from the input a difference between an actual position and the desired position of the corneal anterior surface. A device is in signal communication with the comparator for moving the patient a distance in a direction for matching the actual position to the desired position of the corneal anterior surface.

A method for positioning an eye of a patient comprises the steps of receiving a reflected beam from an anterior surface of a cornea of an eye of a patient. The received reflected beam is compared with a reference beam calibrated to a desired position of the corneal anterior surface. A difference between an actual position and the desired position of the corneal anterior surface is calculated from the comparing step. Then the patient is moved a distance in a direction for matching the actual position to the desired position of the corneal anterior surface.

DETAILED DESCRIPTION OF THE PREFERRED EMBODIMENTS

Figure 1:
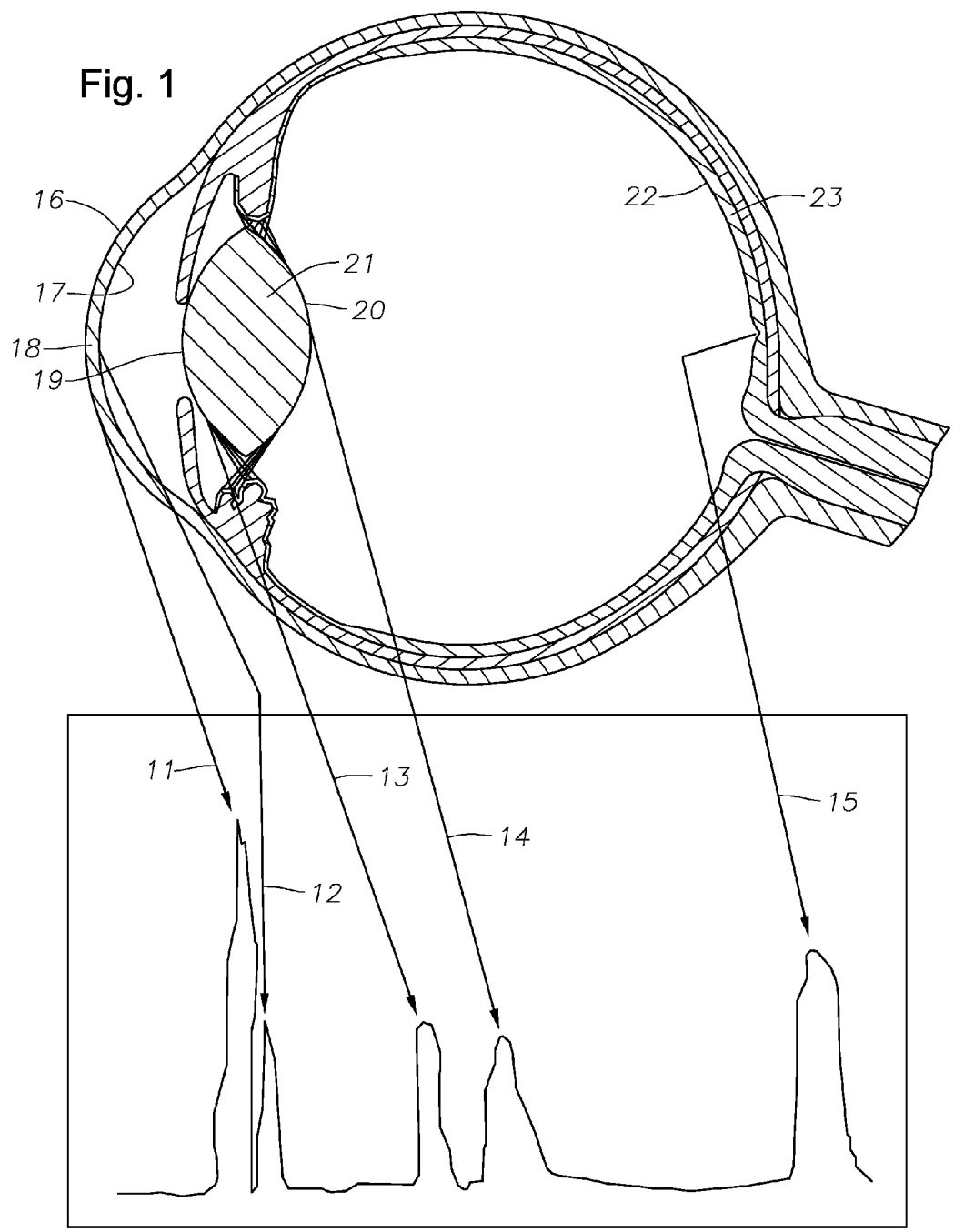
FIG. 1 illustrates reflections from various structures of the eye.
Figure 2:
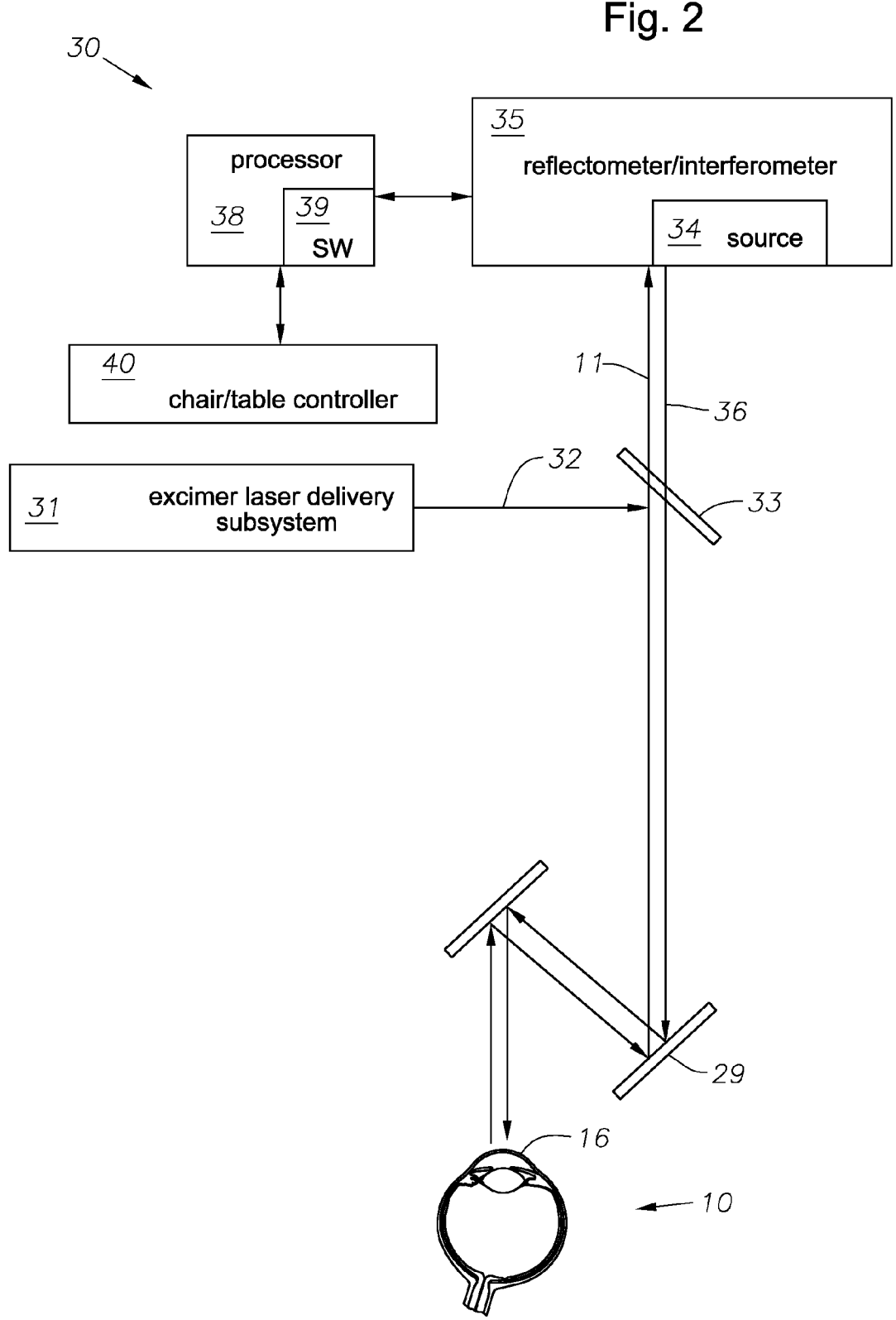
FIG. 2 is a schematic diagram of an exemplary embodiment of the eye positioning system of the present invention.
Figure 3:
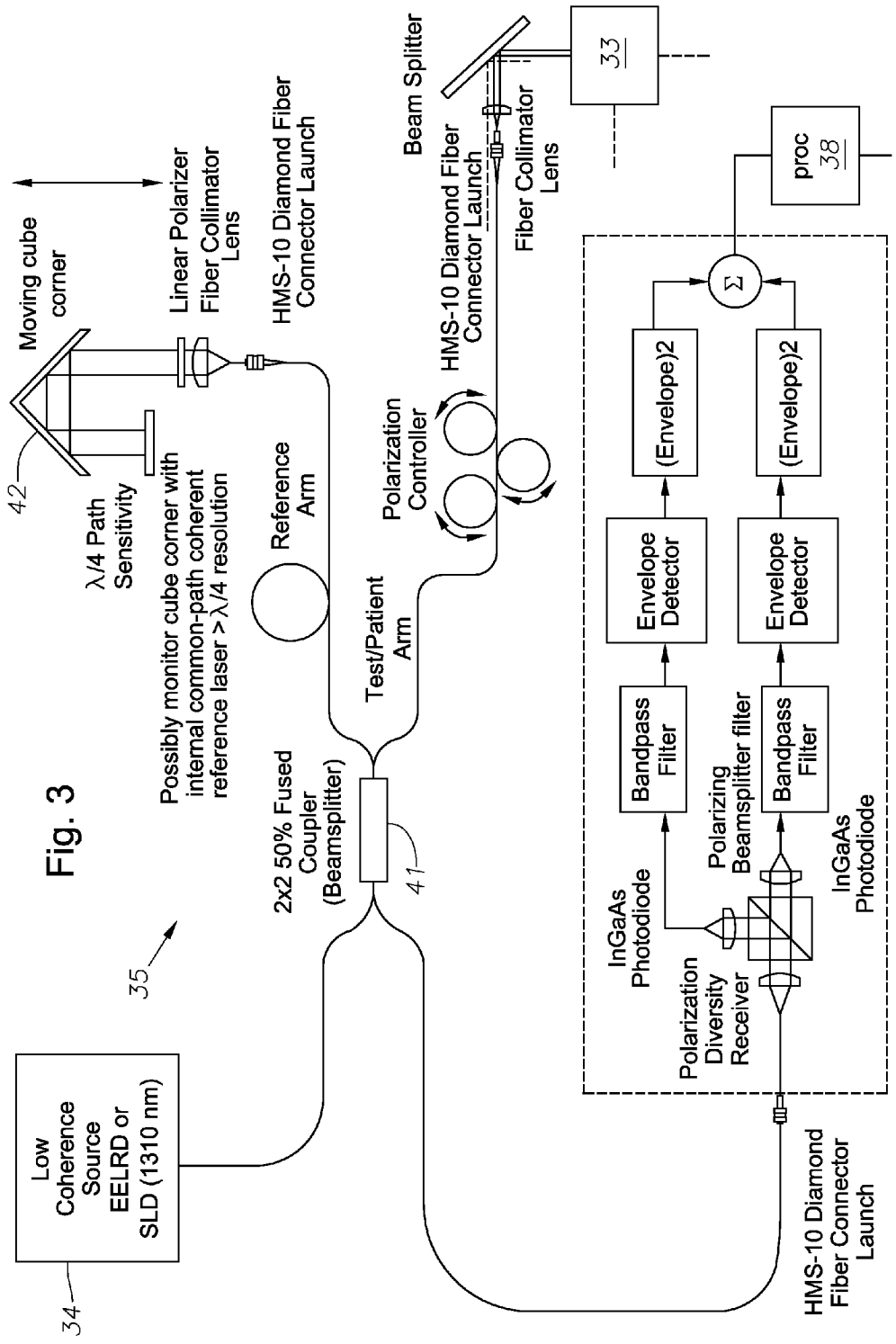
FIG. 3 is a more detailed view of an embodiment of the reflectometer/interferometer.

A description of preferred embodiments of the invention will now be presented with reference to FIGS. 1-3.

The eye 10 (FIG. 1) contains several structures that can reflect light. Depending upon the wavelength and intensity of incoming radiation, reflections 11-15 can be detected, respectively, from the anterior 16 and posterior 17 surfaces of the cornea 18, the anterior 19 and posterior 20 surfaces of the lens 21, and anterior surface 22 of the retina 23. If a broad-bandwidth source is used, reflections 11 from the cornea's anterior surface 16 can be obtained with virtually no contribution from the other reflections 12-15.

A high-level schematic diagram of a system 30 for precisely determining a position of a patient's eye 10 is given in FIG. 2, wherein an excimer laser delivery subsystem 31 is configured to deliver a beam 32 of ablating radiation to the eye 10 after impinging upon a beam combiner 33 and adjusted by galvo scan mirrors 29. It will be understood by one of skill in the art that this subsystem 31 is intended to be exemplary, and that the positioning system 30 of the present invention can be used with other subsystems as well.

A source 34, for example, a broad-bandwidth light source, within a reflectometer/interferometer system 35 emits a beam 36 to the beam combiner 33 and thence to the eye 10.

A reflected beam 11 from the eye's anterior corneal surface 16 travels back through the beam combiner 33 to the reflectometer/interferometer 35, where it is compared with a reference beam to determine whether the eye 10, specifically, the corneal plane 16, is positioned at a predetermined position for the excimer laser system 31. Data are output to a processor 38 having software 39 resident thereon to adjust the patient's position, for example, by way of a chair or table position controller 40. The system 30 can act in closed-loop configuration to continue measuring and adjusting until the predetermined position is reached.

A detailed view of an exemplary configuration for a reflectometer/interferometer system 35 for use with the present invention is shown in FIG. 3, wherein the source 34 enters a coupler/beamsplitter 41. The system 35 will have been calibrated so that the scanning cube 42 has as a center of its scan range is as near to the optimum corneal apex plane as possible. Light 11 reflected from the patient's anterior corneal surface 16 interferes with a reference signal at or near the middle of the scan range of the reference path. This arrangement will give a sensitivity in the range of $\lambda/4$, in the micrometer range.

In use, the patient is nominally positioned, and an auto-z feedback loop can be established wherein the front surface signal 11 is used to position the patient chair or table using controller 40.

One of skill in the art will recognize that other configurations for the reflectometer/interferometer could be used without departing from the spirit of the invention.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical and optical equivalents thereof obvious to those skilled in the art, are set forth in the appended claims.

What is claimed is:

1. A system for positioning an eye of a patient comprising:
   a reflectometer for determining an actual distance of a corneal apex of an eye of a patient relative to an aperture of a laser system from an input comprising a reflected beam from the corneal apex, the reflectometer calibratable to a desired position of the corneal apex;
   a comparator in signal communication with the reflectometer for calculating from the input and a reference beam calibrated to the desired position of the corneal apex a difference between an actual position and the desired position of the corneal apex; and
   a device in signal communication with the comparator for receiving a control loop signal from the comparator and moving the patient a distance in a direction for matching the actual position to the desired position of the corneal apex in response to the control loop signal.

2. The system recited in claim 1, wherein the reflectometer comprises an optical low-coherence interferometer.

3. The system recited in claim 1, wherein the reflectometer comprises a broad-bandwidth light source.

4. The system recited in claim 1, wherein the patient-moving device comprises means for moving a patient support element the distance to achieve the desired position.

5. The system recited in claim 1, wherein the reflectometer and the patient-moving device are connected in a closed-loop feedback configuration.

6. The system recited in claim 1, wherein the comparator comprises a processor having software resident thereon for calculating from the input a signal for being communicated to the patient-moving device to achieve the desired position.

7. A method for positioning an eye of a patient relative to an aperture of a laser system comprising the steps of:
   receiving a reflected beam from a corneal apex of an eye of a patient;
   determining an actual position of the corneal apex with respect to the aperture of the laser system based on the reflected beam;
   comparing the received reflected beam with a reference beam calibrated to a desired position of the corneal apex;
   calculating from the comparing step a difference between the actual position and the desired position of the corneal apex; and
   moving the patient a distance in a direction for matching the actual position to the desired position of the corneal apex.

8. The method recited in claim 7, wherein the receiving and comparing steps are carried out with the use of an optical low-coherence interferometer.

9. The method recited in claim 7, further comprising the step, prior to the receiving step, of directing a broad-bandwidth light source to the corneal apex.

10. The method recited in claim 7, wherein the patient-moving step comprises moving a patient support element the distance to achieve the desired position.

11. The method recited in claim 7, wherein the receiving, comparing, calculating, and moving steps are carried out in a closed-loop feedback method.

12. The method recited in claim 7, wherein the calculating step comprises calculating from the received reflected beam a signal for being communicated to a patient-moving device to achieve the desired position.

* * * * *